United States Patent
Kumar et al.

(10) Patent No.: US 9,861,585 B2
(45) Date of Patent: Jan. 9, 2018

(54) OSMOTIC FLOATING TABLETS

(71) Applicant: RANBAXY LABORATORIES LIMITED, New Delhi, Delhi (IN)

(72) Inventors: Varinder Kumar, Sangrur (IN); Shavej Ahmad, Lucknow (IN); Romi Barat Singh, Varanasi (IN); Ajay Kumar Singla, Gurgaon (IN)

(73) Assignee: SUN PHARMACEUTICAL INDUSTRIES LIMITED, Mumbai (IN)

( * ) Notice: Subject to any disclaimer, the term of this patent is extended or adjusted under 35 U.S.C. 154(b) by 52 days.

(21) Appl. No.: 14/435,777

(22) PCT Filed: Oct. 15, 2013

(86) PCT No.: PCT/IB2013/059374
§ 371 (c)(1),
(2) Date: Apr. 15, 2015

(87) PCT Pub. No.: WO2014/060952
PCT Pub. Date: Apr. 24, 2014

(65) Prior Publication Data
US 2015/0231084 A1  Aug. 20, 2015

(30) Foreign Application Priority Data
Oct. 16, 2012  (IN) .......................... 3222/DEL/2012

(51) Int. Cl.
*A61K 9/28* (2006.01)
*A61J 3/00* (2006.01)
*A61J 3/10* (2006.01)

(52) U.S. Cl.
CPC ............. *A61K 9/2886* (2013.01); *A61J 3/005* (2013.01); *A61J 3/10* (2013.01); *A61K 9/2806* (2013.01); *A61K 9/2893* (2013.01)

(58) Field of Classification Search
CPC .................. A61K 9/28; A61J 3/00; A61J 3/10
USPC ........................................................ 424/475
See application file for complete search history.

(56) References Cited

U.S. PATENT DOCUMENTS

| | | | |
|---|---|---|---|
| 6,207,197 B1 | 3/2001 | Illum et al. ................ 424/491 |
| 2002/0051814 A1 | 5/2002 | Chen ............................ 424/451 |
| 2005/0031688 A1 | 2/2005 | Ayala .......................... 424/473 |
| 2007/0269511 A1 | 11/2007 | Bockbrader et al. ......... 424/468 |
| 2010/0112052 A1* | 5/2010 | Chen ..................... A61K 9/209 424/468 |
| 2010/0255067 A1 | 10/2010 | Sammohi et al. ............ 424/443 |
| 2011/0135723 A1 | 6/2011 | Kshirsagar et al. .......... 424/465 |

FOREIGN PATENT DOCUMENTS

| | | | |
|---|---|---|---|
| EP | 0 662 321 | 10/1999 | ............... A61K 9/00 |
| WO | WO 03/035029 | 5/2003 | ............... A61K 9/00 |
| WO | WO 03/063825 | 8/2003 | ............... A61K 9/00 |
| WO | WO 03063825 A1 * | 8/2003 | |
| WO | WO 2007/078895 | 7/2007 | ............. A01N 33/02 |
| WO | WO 2008/001341 | 1/2008 | ............... A61K 9/00 |
| WO | WO 2011/151708 | 12/2011 | ........... A61K 31/197 |

* cited by examiner

*Primary Examiner* — Johann R Richter
*Assistant Examiner* — Courtney Brown

(57) ABSTRACT

The present invention relates to an osmotic floating tablet comprising: (i) an inner core comprising a drug, one or more low density polymers, and one or more pharmaceutically acceptable excipients; and (ii) an outer osmotic coating surrounding the inner core that is substantially permeable to surrounding fluids and substantially impermeable to the drug. The present invention also relates to processes for the preparation of said tablets.

16 Claims, No Drawings

OSMOTIC FLOATING TABLETS

FIELD OF THE INVENTION

The present invention relates to osmotic floating tablets comprising: (i) an inner core comprising a drug, one or more low density polymers, and one or more pharmaceutically acceptable excipients; and (ii) an outer osmotic coating surrounding the inner core that is substantially permeable to surrounding fluids and substantially impermeable to the drug. The present invention also relates to processes for the preparation of said tablets.

BACKGROUND OF THE INVENTION

Oral administration is the most preferred and convenient route of administration for various types of drugs. However, there are certain drugs that do not have uniform absorption throughout the entire gastrointestinal tract and are predominantly absorbed from the stomach and the upper part of the intestine. For such drugs, it is beneficial to develop oral gastroretentive dosage forms that can remain in the gastric region for longer periods of time so as to significantly prolong the gastric retention time. Such gastroretentive dosage forms are also useful for drugs that are poorly soluble, degraded by the higher pH of the intestine, or have an absorption which is modified by changes in gastric emptying time. Gastroretentive dosage forms are also useful for local as well as sustained drug delivery for certain disease states.

To formulate such stomach-specific gastroretentive dosage forms, several techniques have been described in the prior art such as hydrodynamically balanced systems (HBS)/floating drug delivery system, low density systems, bioadhesive or mucoadhesive systems, high density systems, superporous hydrogels, and magnetic systems.

U.S. Publication No. 2007/0269511 discloses a pregabalin gastroretentive formulation comprising a matrix forming agent and a swelling agent wherein the matrix forming agent is polyvinyl acetate and polyvinylpyrrolidone, and the swelling agent is cross-linked polyvinylpyrrolidone.

PCT Publication No. WO 2011/151708 discloses a gastroretentive dosage form comprising a GABA analog, at least one swelling agent, at least one non-swelling release retardant, and at least one pharmaceutically acceptable excipient.

U.S. Publication No. 2011/0135723 discloses once-daily pharmaceutical compositions of pregabalin wherein the excipients include one or more water-insoluble components or a combination of one or more water-insoluble components and one or more water-soluble components.

U.S. Publication No. 2010/0255067 discloses pharmaceutical compositions comprising pregabalin, a hydrophobic release-controlling agent, and other pharmaceutically acceptable excipients.

PCT Publication No. WO 03/035029 discloses a gastric retentive dosage form consisting of single polymer matrix comprising an active agent and hydrophilic polymers such as hydroxypropyl methylcellulose and poly(ethylene oxide).

U.S. Pat. No. 6,207,197 discloses gastro-retentive controlled-release compositions comprising microspheres containing a drug in an inner core, a rate-controlling layer of a hydrophilic polymer, and an outer layer of bioadhesive cationic polymer.

However, administration of such dosage forms might result in fluctuating drug levels in the plasma. In order to overcome this drawback, the inventors have now developed an osmotic floating tablet comprising: (i) an inner core comprising a drug, one or more low density polymers, and one or more pharmaceutically acceptable excipients; and (ii) an outer osmotic coating surrounding the inner core that is substantially permeable to the surrounding fluids and substantially impermeable to the drug. The incorporation of such an osmotic coating on the floating inner core provides several advantages over conventional gastroretentive dosage forms, such as reduction in the plasma level fluctuations, zero order drug release, and resistance against alcohol-induced dose dumping.

SUMMARY OF THE INVENTION

The present invention relates to an osmotic floating tablet comprising: (i) an inner core comprising a drug, one or more low density polymers, and one or more pharmaceutically acceptable excipients; and (ii) an outer osmotic coating surrounding the inner core that is substantially permeable to the surrounding fluids and substantially impermeable to the drug. The present invention also includes processes for the preparation of said osmotic floating tablet.

DETAILED DESCRIPTION OF THE INVENTION

A first aspect of the present invention provides an osmotic floating tablet comprising:
  (i) an inner core comprising a drug, one or more low density polymers, and one or more pharmaceutically acceptable excipients; and
  (ii) an outer osmotic coating surrounding the inner core that is substantially permeable to surrounding fluids and substantially impermeable to the drug.

According to one embodiment of the above aspect, there is provided an osmotic floating tablet comprising:
  (i) an inner core comprising a drug, one or more low density polymers, and one or more pharmaceutically acceptable excipients; and
  (ii) an outer osmotic coating surrounding the inner core that is substantially permeable to surrounding fluids and substantially impermeable to the drug
wherein one or more low density polymers are selected from the group comprising polyvinyl alcohol-polyethylene glycol graft copolymer, acrylic acid polymer, methacrylic acid copolymers, polyvinyl alcohol, polyvinyl acetate, polysaccharides, cellulose based polymers, or their combinations.

According to another embodiment of the above aspect, there is provided an osmotic floating tablet comprising:
  (i) an inner core comprising a drug, one or more low density polymers, and one or more pharmaceutically acceptable excipients; and
  (ii) an outer osmotic coating surrounding the inner core that is substantially permeable to surrounding fluids and substantially impermeable to the drug
wherein the outer osmotic coating comprises one or more semi-permeable membrane forming polymers, one or more pore-forming agents, and one or more plasticizers.

A second aspect of the present invention provides an osmotic floating tablet comprising:
  (i) an inner core comprising a drug, one or more low density polymers, and one or more pharmaceutically acceptable excipients; and
  (ii) an outer osmotic coating surrounding the inner core that is substantially permeable to surrounding fluids, and substantially impermeable to the drug wherein the tablet further comprises a subcoat layer located between the inner tablet core and the outer osmotic coating.

According to one embodiment of the above aspect, the subcoat layer comprises one or more polymers and one or more lubricants.

A third aspect of the present invention provides a process for the preparation of an osmotic floating tablet wherein the process comprises the steps of:
(i) blending the drug with one or more low density polymers and one or more pharmaceutically acceptable excipients;
(ii) directly compressing the blend of step (i) to form the inner tablet core;
(iii) dissolving/dispersing one or more semi-permeable membrane-forming polymers, one or more pore-forming agents, and one or more plasticizers in a suitable solvent; and
(iv) applying the coating composition of step (iii) over the tablet core of step (ii) to form the osmotic floating tablet.

A fourth aspect of the present invention provides a process for the preparation of an osmotic floating tablet wherein the process comprises the steps of:
(i) blending the drug with one or more low density polymers and one or more pharmaceutically acceptable excipients;
(ii) directly compressing the blend of step (i) to form the inner tablet core;
(iii) dissolving one or more polymers in a suitable solvent followed by dispersion of the lubricant to form a subcoat dispersion;
(iv) applying the subcoat dispersion of step (iii) over the tablet core of step (ii);
(v) dissolving/dispersing one or more semi-permeable membrane-forming polymers, one or more pore-forming agents, and one or more plasticizers in a suitable solvent; and
(vi) applying the coating composition of step (v) over the subcoated tablet core of step (iv) to form the osmotic floating tablet.

The term "osmotic floating tablet", as used herein, represents a tablet designed in such a way so that it is retained in the stomach for a prolonged period of time and is intended to provide zero order drug-release. While the osmotic floating tablet floats over the gastric contents, the drug is released slowly at a desired rate, resulting in an increased gastric retention time. The outer osmotic coating controls the drug-release from the tablet.

Examples of drugs that can be incorporated in the osmotic floating tablet of the present invention include, but are not limited to, pregabalin, losartan, cefuroxime axetil, metformin, trimetazidine dihydrochloride, faropenem, carbidopa, levodopa, methyldopa, verapamil, propranolol, carvedilol, atenolol, albuterol, pirbuterol, nifedipine, nimodipine, nicardipine, amlodipine, prazosin, guanabenz, allopurinol, metoprolol, oxprenolol, baclofen, sumatriptan, benazepril, enalapril, lisinopril, captopril, quinapril, moxipril, indolapril, olindapril, retinapril, spirapril, cilazapril, perindopril, ramipril, zofenopril, fosinopril, nitrofurantoin, acyclovir, valacyclovir, zidovudine, inosine, didanosine, pranobex, tribavirin, vidarabine, simvastatin, pravastatin, atorvastatin, lovastatin, selegiline, midazolam, lithium carbonate, lithium citrate, cimetidine, ranitidine, famotidine, nizatidine, bifentidine, nifentidine, roxatidine, omeprazole, lansoprazole, pentoprazole, magnesium carbonate, aluminum carbonate, aluminum hydroxide, magnesium oxide, sucralfate, carbenoloxalone, misoprostol, pirenzepine, telenzepine, bismuth salts, ciprofloxacin, clarithromycin, amoxicillin, cephalexin, and pharmaceutically acceptable salts, esters, or prodrugs thereof. The dose of any drug is in a therapeutically effective amount to treat a disease or condition.

The term "low density polymers", as used herein, includes polymers that have low bulk density so as to cause the tablet to float, and are non-swelling in nature. Non-swelling behavior can be pH-dependent or pH-independent. Suitable low density polymers include polyvinyl alcohol-polyethylene glycol graft copolymers such as Kollicoat® Protect; acrylic acid polymers such as Carbopol®; methacrylic acid copolymers such as Eudragit® L100, Eudragit® S100, and Eudragit® E PO; polyvinyl alcohol; polyvinyl acetate; polysaccharides such as inulin and pullulan; cellulose based polymers such as hypromellose phthalate, hypromellose succinate, and ethyl cellulose; or combinations thereof.

The core of the present invention comprises one or more pharmaceutically acceptable excipients that are routinely used in pharmaceutical tablets, and are selected from the group comprising diluents, binders, disintegrants, lubricants, glidants, or combinations thereof.

Suitable diluents are selected from the group comprising microcrystalline cellulose, silicified microcrystalline cellulose, microfine cellulose, lactose, starch, pregelatinized starch, calcium carbonate, calcium sulfate, sugar, mannitol, sorbitol, dextrates, dextrin, maltodextrin, dextrose, dibasic calcium phosphate dihydrate, tribasic calcium phosphate, magnesium carbonate, magnesium oxide, or combinations thereof.

Suitable binders are selected from the group comprising polyvinylpyrrolidone, cross-linked polyvinylpyrrolidone, cellulose gums (e.g. carboxymethyl cellulose, hydroxypropyl methylcellulose, and hydroxypropyl cellulose), pregelatinized starch, acacia, guar gum, alginic acid, carbomer, dextrin, maltodextrin, or combinations thereof.

Suitable disintegrants are selected from the group comprising mannitol, alginic acid, carboxymethyl cellulose, hydroxypropyl cellulose, microcrystalline cellulose, croscarmellose sodium, povidone, crospovidone, magnesium aluminum silicate, methylcellulose, sodium alginate, starches, modified starches, or combinations thereof.

Suitable lubricants are selected from the group comprising magnesium stearate, zinc stearate, calcium stearate, stearic acid, sodium stearyl fumarate, vegetable oil, mineral oil, or combinations thereof.

Suitable glidants are selected from the group comprising talc, colloidal silicon dioxide, corn starch, or combinations thereof.

The term "outer osmotic coating", as used herein, refers to a semi-permeable membrane that is substantially permeable to the passage of fluid from the environment to the core allowing water or solvent to pass into the core, and is substantially impermeable to the passage of drug from the inner core. The outer osmotic coating comprises one or more semi-permeable membrane-forming polymers, one or more pore-forming agents, and one or more plasticizers.

Suitable semi-permeable membrane-forming polymers are selected from the group comprising cellulose acetate, cellulose diacetate, cellulose triacetate, cellulose acetate butyrate, cellulose tri-mallitate, ethyl cellulose, methyl methacrylate, or combinations thereof.

Pore-forming agents help to draw water from the surrounding medium into the core, and are selected from the group comprising polyethylene glycol, hydroxymethyl cellulose, hydroxypropyl methyl cellulose, hydroxypropyl cellulose, propylene glycol, polyvinylpyrrolidone, micronized sugar, sodium chloride, mannitol, sorbitol, or combinations thereof.

Suitable plasticizers are selected from the group comprising triacetin, acetylated triacetin, triethyl citrate, dibutyl sebacate, tributyl citrate, glycerol tributyrate, diacetylated monoglyceride, rapeseed oil, olive oil, sesame oil, acetyl tributyl citrate, acetyl triethyl citrate, glycerin sorbitol, diethyl oxalate, diethyl phthalate, diethyl malate, diethyl fumarate, dibutyl succinate, diethyl malonate, dioctyl phthalate, or combinations thereof.

The osmotic floating tablet, as described herein, may further comprise a subcoat layer located between the inner core and the outer osmotic coating. The subcoat layer comprises one or more polymers and one or more lubricants.

Suitable polymers in the subcoat layer are selected from the group comprising hydroxypropyl cellulose, hydroxyethyl cellulose, hydroxypropyl methyl cellulose, polyvinyl pyrrolidone, polyvinyl acetate, or combinations thereof.

Suitable lubricants in the subcoat layer are selected from the group comprising magnesium stearate, calcium stearate, zinc stearate, glyceryl monosterate, sodium stearyl fumarate, polyoxyethylene monostearate, sucrose monolaurate, sodium lauryl sulfate, magnesium lauryl sulfate, magnesium dodecyl sulfate, or combinations thereof.

Examples of solvents used for granulation or coating include purified water and organic solvents such as acetone, ethanol, isopropyl alcohol, methylene chloride, or combinations thereof.

The inner tablet core may be prepared by conventional techniques known in the art such as such as direct compression, wet granulation, or dry granulation. The resultant blends/granules can be compressed into a tablet using a conventional tableting process. Preferably, the inner tablet core is prepared by the technique of direct compression.

Coating may be performed by applying the coating composition as a solution/suspension/blend using any conventional coating technique known in the art such as spray coating in a conventional coating pan, a fluidized bed processor, dip coating, or compression coating.

The outer osmotic coating layer of the tablets may additionally comprise one or more orifices that is created through the semi-permeable membrane and allows the inner tablet core to communicate with the surrounding media. The orifice may be created by mechanical perforation, laser perforation, or formed in response to the osmotic pressure acting on the tablet.

The following examples represent various embodiments according to the present invention. The examples are given solely for the purpose of illustration and are not to be construed as limitations of the present invention, as many variations thereof are possible without departing from the spirit and scope of the invention.

EXAMPLES 1-3

| S. No. | Ingredients | Quantity (mg/tablet) | | |
|---|---|---|---|---|
| | | Example 1 | Example 2 | Example 3 |
| Core tablet | | | | |
| 1. | Pregabalin | 600.00 | 600.00 | 600.00 |
| 2. | Kollicoat ® Protect | 140.00 | 250.00 | 250.00 |
| 3. | Carbopol ® | 250.00 | — | — |
| 4. | Ethyl cellulose | — | 140.00 | — |
| 5. | Eudragit ® E PO | — | — | 140.00 |
| 6. | Magnesium stearate | 10.00 | 10.00 | 10.00 |
| Core weight | | 1000.00 | 1000.00 | 1000.00 |
| Subcoat | | | | |
| 7. | Hydroxypropyl cellulose | 16.25 | 16.25 | 16.25 |
| 8. | Magnesium stearate | 8.75 | 8.75 | 8.75 |
| 9. | Ethanol | q.s. | q.s. | q.s. |
| Weight of subcoat | | 25.00 | 25.00 | 25.00 |
| Osmotic coat | | | | |
| 10. | Cellulose acetate | 33.30 | 33.30 | 33.30 |
| 11. | Polyethylene glycol 6000 | 7.69 | 7.69 | 7.69 |
| 12. | Polyethylene glycol 400 | 5.13 | 5.13 | 5.13 |
| 13. | Triacetin | 5.13 | 5.13 | 5.13 |
| 14. | Acetone | q.s. | q.s. | q.s. |
| 15. | Purified water | q.s. | q.s. | q.s. |
| Weight of osmotic coat | | 51.25 | 51.25 | 51.25 |
| Weight of coated tablet | | 1076.25 | 1076.25 | 1076.25 |

Procedure:
1. Pregabalin was blended with Kollicoat® Protect and Carbopol®/Ethyl cellulose/Eudragit® E PO for 15 minutes.
2. Magnesium stearate was mixed with the blend of step 1.
3. The blend of step 2 was directly compressed using suitable tooling to form an inner tablet core.
4. Hydroxypropyl cellulose was dissolved in ethanol under continuous stirring followed by dispersion of magnesium stearate to form a subcoat dispersion.
5. The tablet core of step 3 was coated with the subcoat dispersion of step 4.
6. Cellulose acetate was dissolved in a mixture of acetone and water.
7. Polyethylene glycol 6000, polyethylene glycol 400, and triacetin were dissolved in the solution of step 6 to form the osmotic coating solution.
8. The subcoated tablets of step 5 were coated with the osmotic coating solution of step 7 until the desired tablet weight was obtained.

EXAMPLE 4

| S. No. | Ingredients | Quantity (mg/tablet) Example 4 |
|---|---|---|
| Core tablet | | |
| 1. | Losartan potassium | 100.00 |
| 2. | Kollicoat ® Protect | 200.00 |
| 3. | Eudragit ® E PO | 155.00 |
| 4. | Pearlitol ® 200SD | 40.00 |
| 5. | Silicon dioxide | 2.50 |
| 6. | Magnesium stearate | 2.50 |
| Core weight | | 500.00 |
| Subcoat | | |
| 7. | Hydroxypropyl cellulose | 6.50 |
| 8. | Magnesium stearate | 3.50 |
| 9. | Ethanol | q.s. |
| Weight of subcoat | | 10.00 |

-continued

| S. No. | Ingredients | Quantity (mg/tablet) Example 4 |
|---|---|---|
| Osmotic coat | | |
| 10. | Cellulose acetate | 19.50 |
| 11. | Polyethylene glycol 6000 | 4.50 |
| 12. | Polyethylene glycol 400 | 3.00 |
| 13. | Triacetin | 3.00 |
| 14. | Acetone | q.s. |
| 15. | Purified water | q.s. |
| Weight of osmotic coat | | 30.00 |
| Weight of coated tablet | | 540.00 |

Procedure:
1. Losartan potassium was blended with Kollicoat® Protect, Eudragit® E PO, Pearlitol® 200SD, and silicon dioxide for 15 minutes.
2. Magnesium stearate was mixed with the blend of step 1.
3. The blend of step 2 was directly compressed using suitable tooling to form an inner tablet core.
4. Hydroxypropyl cellulose was dissolved in ethanol under continuous stirring followed by dispersion of magnesium stearate to form a subcoat dispersion.
5. The tablet core of step 3 was coated with the subcoat dispersion of step 4.
6. Cellulose acetate was dissolved in a mixture of acetone and water.
7. Polyethylene glycol 6000, polyethylene glycol 400, and triacetin were dissolved in the solution of step 6 to form the osmotic coating solution.
8. The subcoated tablets of step 5 were coated with the osmotic coating solution of step 7 until the desired tablet weight was obtained.

EXAMPLE 5

| S. No. | Ingredients | Quantity (mg/tablet) Example 5 |
|---|---|---|
| Core tablet | | |
| 1. | Cefuroxime axetil | 500.00 |
| 2. | Kollicoat ® Protect | 240.00 |
| 3. | Eudragit ® E PO | 160.00 |
| 4. | Pearlitol ® 200SD | 85.00 |
| 5. | Ferric oxide red | 5.00 |
| 6. | Silicon dioxide | 5.00 |
| 7. | Magnesium stearate | 5.00 |
| Core weight | | 1000.00 |
| Subcoat | | |
| 8. | Hydroxypropylcellulose | 13.00 |
| 9. | Magnesium stearate | 7.00 |
| 10. | Ethanol | q.s. |
| Weight of subcoat | | 20.00 |
| Osmotic coat | | |
| 11. | Cellulose acetate | 39.00 |
| 12. | Polyethylene glycol 6000 | 9.00 |
| 13. | Polyethylene glycol 400 | 6.00 |
| 14. | Triacetin | 6.00 |
| 15. | Acetone | q.s. |
| 16. | Purified water | q.s. |
| Weight of osmotic coat | | 60.00 |
| Weight of coated tablet | | 1080.00 |

Procedure:
1. Cefuroxime axetil was blended with Kollicoat® Protect, Eudragit® E PO, Pearlitol® 200SD, ferric oxide red, and silicon dioxide for 15 minutes.
2. Magnesium stearate was mixed with the blend of step 1.
3. The blend of step 2 was directly compressed using suitable tooling to form an inner tablet core.
4. Hydroxypropyl cellulose was dissolved in ethanol under continuous stirring followed by dispersion of magnesium stearate to form a subcoat dispersion.
5. The tablet core of step 3 was coated with the subcoat dispersion of step 4.
6. Cellulose acetate was dissolved in a mixture of acetone and water.
7. Polyethylene glycol 6000, polyethylene glycol 400, and triacetin were dissolved in the solution of step 6 to form the osmotic coating solution.
8. The subcoated tablets of step 5 were coated with the osmotic coating solution of step 7 until the desired tablet weight was obtained.

EXAMPLE 6

| S. No. | Ingredients | Quantity (mg/tablet) Example 6 |
|---|---|---|
| Core tablet | | |
| 1. | Metformin | 500.00 |
| 2. | Kollicoat ® Protect | 240.00 |
| 3. | Eudragit ® E PO | 160.00 |
| 4. | Pearlitol ® 200SD | 90.00 |
| 5. | Silicon dioxide | 5.00 |
| 6. | Magnesium stearate | 5.00 |
| Core weight | | 1000.00 |
| Subcoat | | |
| 7. | Hydroxypropyl cellulose | 13.00 |
| 8. | Magnesium stearate | 7.00 |
| 9. | Ethanol | q.s. |
| Weight of subcoat | | 20.00 |
| Osmotic coat | | |
| 10. | Cellulose acetate | 39.00 |
| 11. | Polyethylene glycol 6000 | 9.00 |
| 12. | Polyethylene glycol 400 | 6.00 |
| 13. | Triacetin | 6.00 |
| 14. | Acetone | q.s. |
| 15. | Purified water | q.s. |
| Weight of osmotic coat | | 60.00 |
| Weight of coated tablet | | 1080.00 |

Procedure:
1. Metformin was blended with Kollicoat® Protect, Eudragit® E PO, Pearlitol® 200SD, and silicon dioxide for 15 minutes.
2. Magnesium stearate was mixed with the blend of step 1.
3. The blend of step 2 was directly compressed using suitable tooling to form an inner tablet core.
4. Hydroxypropyl cellulose was dissolved in ethanol under continuous stirring followed by dispersion of magnesium stearate to form a subcoat dispersion.
5. The tablet core of step 3 was coated with the subcoat dispersion of step 4.
6. Cellulose acetate was dissolved in a mixture of acetone and water.

7. Polyethylene glycol 6000, polyethylene glycol 400, and triacetin were dissolved in the solution of step 6 to form the osmotic coating solution.
8. The subcoated tablets of step 5 were coated with the osmotic coating solution of step 7 until the desired tablet weight was obtained.

EXAMPLE 7

| S. No. | Ingredients | Quantity (mg/tablet) Example 7 |
|---|---|---|
| | Core tablet | |
| 1. | Trimetazidine dihydrochloride | 70.00 |
| 2. | Kollicoat ® Protect | 172.50 |
| 3. | Eudragit ® E PO | 150.00 |
| 4. | Pearlitor ® 200SD | 100.00 |
| 5. | Ferric oxide red | 2.50 |
| 6. | Silicon dioxide | 2.50 |
| 7. | Magnesium Stearate | 2.50 |
| | Core weight | 500.00 |
| | Subcoat | |
| 8. | Hydroxypropyl cellulose | 6.50 |
| 9. | Magnesium stearate | 3.50 |
| 10. | Ethanol | q.s. |
| | Weight of subcoat | 10.00 |
| | Osmotic coat | |
| 11. | Cellulose acetate | 19.50 |
| 12. | Polyethylene glycol 6000 | 4.50 |
| 13. | Polyethylene glycol 400 | 3.00 |
| 14. | Triacetin | 3.00 |
| 15. | Acetone | q.s. |
| 16. | Purified water | q.s. |
| | Weight of osmotic coat | 30.00 |
| | Weight of coated tablet | 540.00 |

Procedure:
1. Trimetazidine dihydrochloride was blended with Kollicoat® Protect, Eudragit® E PO, Pearlitol® 200SD, ferric oxide red, and silicon dioxide for 15 minutes.
2. Magnesium stearate was mixed with the blend of step 1.
3. The blend of step 2 was directly compressed using a suitable tooling to form an inner tablet core.
4. Hydroxypropyl cellulose was dissolved in ethanol under continuous stirring followed by dispersion of magnesium stearate to form a subcoat dispersion.
5. The tablet core of step 3 was coated with the subcoat dispersion of step 4.
6. Cellulose acetate was dissolved in a mixture of acetone and water.
7. Polyethylene glycol 6000, polyethylene glycol 400, and triacetin were dissolved in the solution of step 6 to form the osmotic coating solution.
8. The subcoated tablets of step 5 were coated with the osmotic coating solution of step 7 until the desired tablet weight was obtained.

In-Vitro Studies

The tablets prepared according to Examples 4-7 were subjected to dissolution studies in 900 mL of 0.1N HCl using a USP type II apparatus with a paddle speed at 50 rpm. The results of the release studies are represented in Table 1 below.

TABLE 1

Percentage (%) of In-Vitro Drug Release in USP Type II Apparatus (Media: 900 mL of 0.1N HCl at 50 rpm) from Tablets Prepared According to Examples 4-7

| Time | Drug dissolved (Percent w/w) | | | |
|---|---|---|---|---|
| (hours) | Example 4 | Example 5 | Example 6 | Example 7 |
| 1 | 1 | 2 | 19 | 22 |
| 2 | 8 | 3 | 38 | 35 |
| 4 | 21 | 7 | 58 | 56 |
| 6 | 40 | 27 | 67 | 57 |
| 8 | 53 | 32 | 83 | 82 |
| 12 | 77 | 54 | 97 | 96 |
| 16 | 96 | 71 | 104 | 98 |
| 20 | 104 | 82 | 104 | 101 |

We claim:
1. An osmotic floating tablet consisting of:
an inner core consisting of a drug; one or more low density polymers, and one or more pharmaceutically acceptable excipients selected from the group consisting of diluents, binders, disintegrants, lubricants, glidants, or combinations thereof; and
(ii) an outer osmotic coating consisting of one or more semi-permeable membrane-forming polymers, one or more pore-forming agents, and one or more plasticizers.

2. The osmotic floating tablet of claim 1, wherein the drug is selected from the group comprising pregabalin, losartan, cefuroxime axetil, metformin, trimetazidine dihydrochloride, faropenem, carbidopa, levodopa, methyldopa, verapamil, propranolol, carvedilol, atenolol, albuterol, pirbuterol, nifedipine, nimodipine, nicardipine, amlodipine, prazosin, guanabenz, allopurinol, metoprolol, oxprenolol, baclofen, sumatriptan, benazepril, enalapril, lisinopril, captopril, quinapril, moxipril, indolapril, olindapril, retinapril, spirapril, cilazapril, perindopril, ramipril, zofenopril, fosinopril, nitrofurantoin, acyclovir, valacyclovir, zidovudine, inosine, didanosine, pranobex, tribavirin, vidarabine, simvastatin, pravastatin, atorvastatin, lovastatin, selegiline, midazolam, lithium carbonate, lithium citrate, cimetidine, ranitidine, famotidine, nizatidine, bifentidine, nifentidine, roxatidine, omeprazole, lansoprazole, pentoprazole, magnesium carbonate, aluminum carbonate, aluminum hydroxide, magnesium oxide, sucralfate, carbenoloxalone, misoprostol, pirenzepine, telenzepine, bismuth salts, ciprofloxacin, clarithromycin, amoxicillin, cephalexin, and pharmaceutically acceptable salts, esters, or prodrugs thereof.

3. The osmotic floating tablet of claim 1, wherein the one or more low density polymers are selected from the group comprising polyvinyl alcohol-polyethylene glycol graft copolymers, acrylic acid polymers, methacrylic acid copolymers, polyvinyl alcohol, polyvinyl acetate, polysaccharides, cellulose based polymers, or combinations thereof.

4. The osmotic floating tablet of claim 1, wherein the one or more semi-permeable membrane-forming polymers in the outer osmotic coating are selected from the group comprising cellulose acetate, cellulose diacetate, cellulose triacetate, cellulose acetate butyrate, cellulose tri-mallitate, ethyl cellulose, methyl methacrylate, or combinations thereof.

5. The osmotic floating tablet of claim 1, wherein the one or more pore-forming agents in the outer osmotic coating are selected from the group comprising polyethylene glycol, hydroxymethyl cellulose, hydroxypropyl methylcellulose, hydroxypropyl cellulose, propylene glycol, polyvinylpyrrolidone, micronized sugar, sodium chloride, mannitol, sorbitol, or combinations thereof.

6. The osmotic floating tablet of claim 1, wherein the one or more plasticizers in the outer osmotic coating are selected from the group comprising triacetin, acetylated triacetin, triethylcitrate, dibutylsebacate, tributylcitrate, glyceroltributyrate, diacetylated monoglyceride, rapeseed oil, olive oil, sesame oil, acetyl tributyl citrate, acetyl triethyl citrate, glycerin sorbitol, diethyl oxalate, diethyl phthalate, diethyl malate, diethyl fumarate, dibutyl succinate, diethyl malonate, dioctyl phthalate, or combinations thereof.

7. A process for the preparation of the osmotic floating tablet of claim 1, wherein the process consisting of the steps of:
(i) blending a drug with one or more low density polymers and one or more pharmaceutically acceptable excipients selected from the group consisting of diluents, binders, disintegrants, lubricants, glidants, or combinations thereof;
(ii) directly compressing the blend of step (i) to form an inner tablet core;
(iii) dissolving/dispersing one or more semi-permeable membrane-forming polymers, one or more pore-forming agents, and one or more plasticizers in a suitable solvent; and
(iv) applying the coating composition of step (iii) over the inner tablet core of step (ii) to form the osmotic floating tablet.

8. An osmotic floating tablet consisting of:
(i) an inner core consisting of a drug; one or more low density polymers, and one or more pharmaceutically acceptable excipients selected from the group consisting of diluents, binders, disintegrants, lubricants, glidants, or combinations thereof;
(ii) a subcoat layer comprising one or more polymers and one or more lubricants; and
(iii) an outer osmotic coating consisting of one or more semi-permeable membrane-forming polymers, one or more pore-forming agents, and one or more plasticizers.

9. A process for the preparation of the osmotic floating tablet of claim 8, wherein the process consisting of the steps of:
(i) blending a drug with one or more low density polymers and one or more pharmaceutically acceptable excipients selected from the group consisting of diluents, binders, disintegrants, lubricants, glidants, or combinations thereof;
(ii) directly compressing the blend of step (i) to form an inner tablet core;
(iii) dissolving one or more polymers in a suitable solvent followed by dispersion of the lubricant to form a subcoat dispersion;
(iv) applying the subcoat dispersion of step (iii) over the tablet core of step (ii);
(v) dissolving/dispersing one or more semi-permeable membrane-forming polymers, one or more pore-forming agents, and one or more plasticizers in a suitable solvent; and
(iv) applying the coating composition of step (v) over the subcoated tablet core of step (iv) to form the osmotic floating tablet.

10. The osmotic floating tablet of claim 8, wherein:
the inner core consists of the drug; the one or more low density polymers consist of a polyvinyl alcohol-polyethylene glycol copolymer, acrylic acid polymer, ethyl cellulose and methacrylic acid copolymer, and the lubricant;
(ii) the subcoat layer consists of hydroxypropyl cellulose as the one or more polymers and one or more lubricants; and
(iii) an outer osmotic coating consisting of cellulose acetate as the one or more semi-permeable membrane-forming polymers, polyethylene glycol as the one or more pore-forming agents, and one or more plasticizers.

11. The osmotic floating tablet of claim 10, wherein:
(i) the inner core consists of about 60 wt % drug, about 14-25 wt % polyvinyl alcohol-polyethylene glycol copolymer, about 14-25 wt % acrylic acid polymer, ethyl cellulose, or methacrylic acid copolymer, and a lubricant;
(ii) the subcoat layer consists of about 65 wt % hydroxypropyl cellulose as the one or more polymers and about 35 wt % lubricants; and
(iii) an outer osmotic coating consisting of about 65 wt % cellulose acetate as the one or more semi-permeable membrane-forming polymers, about 25 wt % polyethylene glycol as the one or more pore-forming agents, and one or more plasticizers.

12. The osmotic floating tablet of claim 8, wherein:
(i) the inner core consists of about 20 wt % drug, about 40 wt % polyvinyl alcohol-polyethylene glycol copolymer, about 31 wt % acrylic acid polymer, mannitol, a and a lubricant;
(ii) the subcoat layer consists of about 65 wt % hydroxypropyl cellulose as the one or more polymers and about 35 wt % lubricants; and
(iii) an outer osmotic coating consisting of about 65 wt % cellulose acetate as the one or more semi-permeable membrane-forming polymers, about 25 wt % polyethylene glycol as the one or more pore-forming agents, and one or more plasticizers.

13. The osmotic floating tablet of claim 1, wherein the low density polymer consists of a non-swelling cellulose polymer.

14. The osmotic floating tablet of claim 13, wherein the low density non-swelling cellulose polymer comprises one or more of hypromellose phthalate, hypomellose succinate and ethyl cellulose.

15. The osmotic floating tablet of claim 8, wherein the low density polymer consists of a non-swelling cellulose polymer.

16. The osmotic floating tablet of claim 15, wherein the low density non-swelling cellulose polymer comprises one or more of hypromellose phthalate, hypomellose succinate and ethyl cellulose.

* * * * *